United States Patent
Thomas

(10) Patent No.: US 7,832,292 B2
(45) Date of Patent: Nov. 16, 2010

(54) POLAR COORDINATE POSITIONING SYSTEM

(75) Inventor: Richard A. Thomas, Miami, FL (US)

(73) Assignee: NPE Systems, Inc., Pembroke Pines, FL (US)

( * ) Notice: Subject to any disclaimer, the term of this patent is extended or adjusted under 35 U.S.C. 154(b) by 645 days.

(21) Appl. No.: 11/804,721

(22) Filed: May 18, 2007

(65) Prior Publication Data

US 2009/0064519 A1    Mar. 12, 2009

Related U.S. Application Data

(60) Provisional application No. 60/802,057, filed on May 19, 2006.

(51) Int. Cl.
*G01N 35/02* (2006.01)
*G01N 35/10* (2006.01)

(52) U.S. Cl. .................... 73/864.23; 73/864.24; 422/64

(58) Field of Classification Search . 73/864.23–864.25; 422/65

See application file for complete search history.

(56) References Cited

U.S. PATENT DOCUMENTS

| | | | |
|---|---|---|---|
| 4,673,288 A | 6/1987 | Thomas et al. | |
| 4,818,103 A | 4/1989 | Thomas et al. | |
| 6,148,680 A * | 11/2000 | Baeuerle et al. | .......... 73/864.25 |
| 6,587,792 B1 | 7/2003 | Thomas | |
| 6,652,724 B2 | 11/2003 | Michael et al. | |
| 6,855,553 B1 | 2/2005 | Bedingham et al. | |
| 2005/0118066 A1* | 6/2005 | Ikeda et al. | .................. 422/100 |
| 2007/0085997 A1 | 4/2007 | Thomas | |

FOREIGN PATENT DOCUMENTS

JP      62184356 A  *  8/1987
WO    WO/2007/044617    4/2007

OTHER PUBLICATIONS

MDrive™ Plus Motion Control Hardware Reference Revision R031706, Intelligent Motion Systems, Inc., Marlborough, CT, Mar. 2006, pp. 1-101 preceded by 2 unnumbered pages and followed by 2 unnumbered pages.

* cited by examiner

*Primary Examiner*—Thomas P Noland
(74) *Attorney, Agent, or Firm*—McDermott Will & Emery LLP

(57) ABSTRACT

The present disclosure provides a polar coordinate positioning system. The system can be used, for example, to sample a microtiter plate or sample tubes. In some embodiments, the system orients a sample with respect to a sampling tool using polar coordinates. In some embodiments, the sample is configured to rotate about an axis and move linearly in a direction transverse to the axis, and the sampling tool is configured to move linearly in a direction transverse to the linearly movement of the sample.

6 Claims, 7 Drawing Sheets

POLAR COORDINATE POSITIONING SYSTEM

RELATED APPLICATIONS

This application claims priority benefit from U.S. Provisional Application No. 60/802,057, filed May 19, 2006, the entirety of which is incorporated herein by reference.

BACKGROUND OF THE INVENTION

1. Field of the Invention

This disclosure relates to a system for handling samples, and in particular, this disclosure relates to a polar coordinate positioning system.

2. Background of Prior Art

Test tubes and sample cups, also referred to as sample tubes, have long been the method of choice in handling samples. The use of various shaped racks to hold multiple sample tubes has helped in the automation of sample preparation and analysis. Many devices move sample tube racks from a load point to the sampling position or move the sample racks from station to station where sample loading, sampling or reagent addition takes place.

The microplate, also referred to as a microtiter plate or multiwell plate, has become an integral tool used in biology, cellular research, drug discovery research, and a host of other applications, and it is particularly useful in high throughput screening assays. It has allowed automation of many of the steps required for sample preparation and analysis. The geometry of the microplate well arrays have a layout of rows and columns. The 96 well plate, for example, has twelve rows and eight columns. This geometry naturally lends itself to the use of robots that are actuated in a Cartesian coordinate system (x, y). One or more of the sample wells in the plate is positioned to the correct location in an x-y plane where reagents are added to the well or wells, or sample is removed from the well or wells for analysis, by a single or multi-head sampling station.

The X and Y axis motions are usually controlled by motors that are coupled to the microplate holder by some combination of gears, belts, pulleys, cables, or lead screws in combination with a rail-bearing system to control the motion in each axis. The motors are used in combination with an open loop or closed loop control system. A series of switches, sensors, or encoders are used to define the zero point of the positioning and keep track of the location relative to the zero point. Some systems use linear actuators to position, thereby combining the rail-bearing and motor in a single unit.

SUMMARY OF INVENTION

Due to the widespread need to assay multiple samples, it would be advantageous to develop a more efficient and cost effective system to assay multiple samples. The present disclosure satisfies this need and provides related advantages as well.

The present disclosure provides a polar coordinate positioning system that can be used, for example, to sample a microtiter plate or sample tubes. In some embodiments, a positioning system is described, based on polar or cylindrical coordinates, which includes a sampling needle for obtaining a sample, the sampling needle being movable in a first direction; and a sampling tray that comprises at least one sampling well, the sampling tray being movable in a second direction that is transverse to the first direction, the sampling tray further being rotatable about an axis that is transverse to the second direction. The sampling needle is preferably configured to obtain the sample from the at least one sampling well, and the sampling tray is oriented and positioned with respect to an angular displacement about the axis and a radial displacement from an origin.

In some embodiments, the positioning system includes a first motor that is coupled to the sampling tray for orienting the sampling tray about the axis. The first motor preferably moves with the sampling tray in the second direction.

In some embodiments, the second direction is substantially linear, and in some embodiments, the first direction is substantially linear.

Some embodiments include a second motor is configured to move the sampling tray in the second direction. The second motor preferably moves the sampling tray in the second direction with less than or equal to about one rotation of a first cam.

In some embodiments, a third motor is configured to move the sampling needle in the first direction. The third motor preferably moves the sampling tray in the first direction with less than about one rotation of a second cam.

In some embodiments, the sampling tray is configured to move along the path of an arc. In further embodiments, the sampling tray further comprises a reagent tube. In yet further embodiments, the sampling tray is configured to serially orient a reagent tube with the sampling needle and orient the sampling tray with a sampling well.

Some embodiments disclosed herein are directed to a system for positioning a sample relative to a sampling tool that, the system including a first driving means for imparting one of angular or radial displacement on a sample and a second driving means for imparting the other of angular or radial displacement on the sample. The first driving means and the second driving means are preferably configured to orient, through the angular and radial displacement, a sampling tool with respect to the sample.

In some embodiments, the sample is at least one of a sample tube, a sample cup, an array of sample tubes, an array of sample cups, and a micro plate. In further embodiments described herein, at least one of either the first driving means and the second driving means comprises an intelligent motor with a self-contained encoder and microprocessor. Some embodiments provide that radial displacement is provided by a motor in conjunction with a cam that is configured to rotate less than or equal to about 360 degrees.

Some embodiments are directed to various methods. In some embodiments a method is disclosed for positioning an sample from a first position to a second position. The method preferably includes the steps of rotating a sample about an axis to provide angular displacement of the sample and linearly moving the sample with respect to a sampling tool to provide radial displacement of the sample. The axis is preferably transverse to the linearly movement of the sample.

In some embodiments, the method provides that rotating the sample and linearly moving the sample occur simultaneously. In further embodiments of the method include the step of moving the sampling tool with respect to the sample. In yet further embodiments, movement of the sampling tool is transverse to the direction of linear movement.

BRIEF DESCRIPTION OF THE DRAWINGS

The preferred embodiments of the present disclosure and methods of relating to their uses and illustrating their features will now be discussed in detail. These drawings depict embodiments in the accompanying drawings, which are for illustrative purposes only, and are not to limit of the scope of this disclosure.

DETAILED DESCRIPTION OF THE INVENTION

Figure 1:
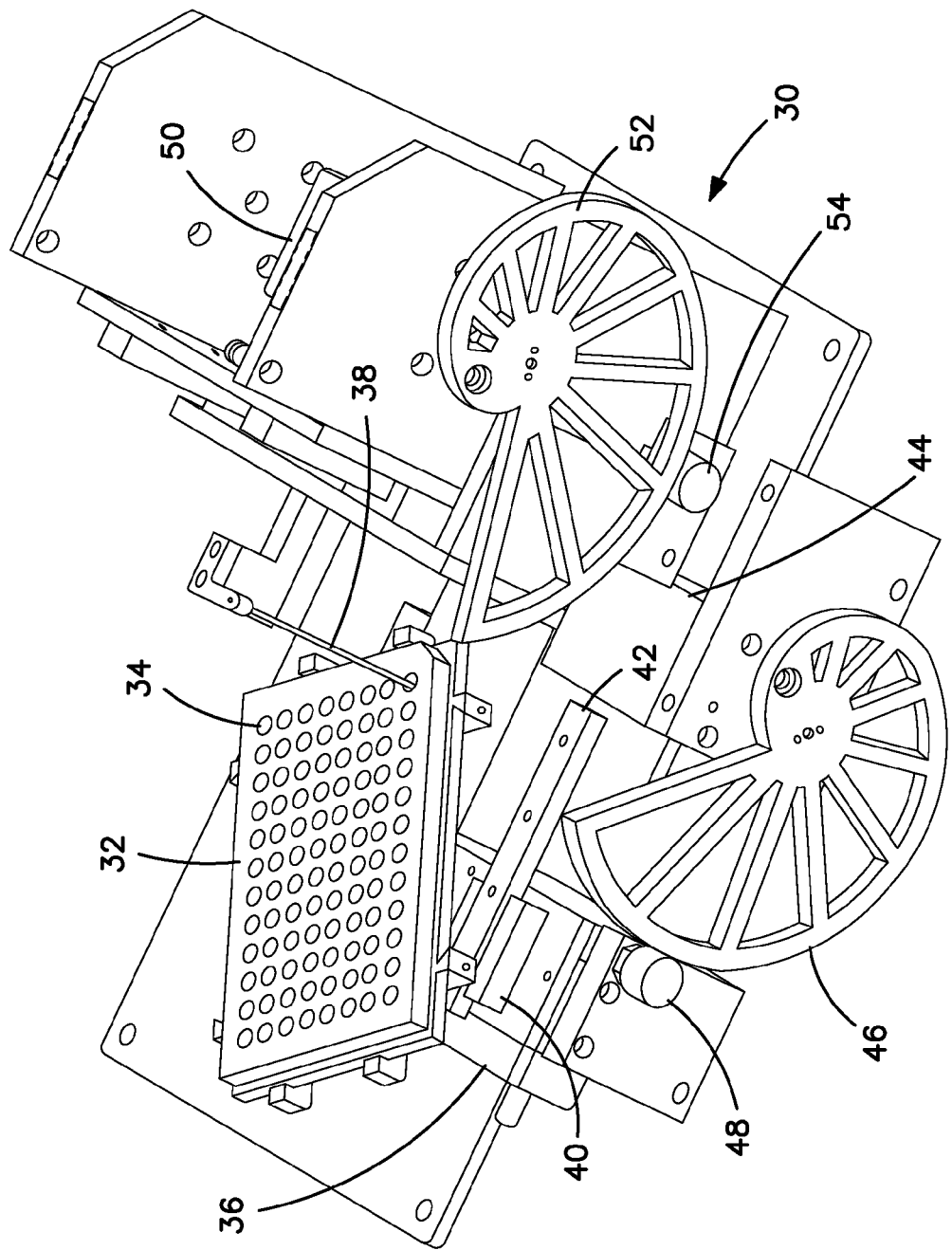
FIG. 1 illustrates a perspective view of one embodiment of a polar coordinate positioning system, as described herein.

The disclosure provides a unique positioning system that uses polar coordinates rather than Cartesian coordinates to locate a point in a plane. This system may be used to position microplates or sample tubes with respect to a sampling head, or a sampling head with respect to the microplates or sample tubes. In addition, the positioning system may be used for a microscope, or other systems that require the movement of a stage to a specific location in space.

As used herein, in a "polar coordinate positioning system (r,θ)," the polar plane consists of a reference axis, or ray, that emanates from a point called the origin. Positions or coordinates are determined according to the distance or radius, from the origin, symbolized by "r," and the angle relative to the reference axis, symbolized by the lowercase Greek theta (θ).

As used herein, in a "Cartesian coordinate positioning system (x, y)," cartesian coordinates (x,y) specify the position of a point in a plane relative to the horizontal x and the vertical y axes. The x and y axes form the basis of a two-dimensional Cartesian coordinate system.

In a polar coordinate positioning system of the disclosure used to manipulate a microplate or sample cup, the location of the well in the microplate, or the sample cup in a plane, may be uniquely defined by an angle and radial displacement from an axis of rotation perpendicular to the plane. This may be accomplished by rotating the microplate or the sample tube rack with respect to the sampling head thus providing the angular displacement and then moving the microplate or the sample tube rack with respect to a fixed sampling head to provide the radial displacement or moving the sampling head providing the radial displacement with respect to the microplate, sample cup or the sample tube, or a combination of both. The sampling head may access more than one well or tube at a time.

In some embodiments, the sampling needle location is fixed in the plane of the microplate, sample cup, or sample tube holder and attaches the microplate, the sample cup holder or sample tube holder to the axis of rotation of a motor. The rotation of the motor provides the angular displacement. The other axis that provides the radius radial displacement is a single axis linear motion system that moves the microplate, sample cup or sample tube holder. The radius motion axis may be driven by a linear motor, or some combination of gears, belts, pulleys, cables, or lead screw in combination with a rail-bearing system to control the motion.

The polar coordinate positioning system of the disclosure can be modified. In some embodiments, the microplate, sample cup or sample tube holder can be attached directly to the motor, which eliminates one entire linear axis along with the rail-bearing system, and zero detection switches. These embodiments reduce the complexity of the positioning system, producing significant reductions in costs and increased system reliability. A polar coordinate positioning system can be further simplified by using a cam to drive the radial motion axis.

A further reduction in complexity can be achieved if the cam is driven directly by a motor with sufficient angular resolution to accomplish the entire range of motion in less than one complete rotation of the motor. If the motor has an encoder, then there will be an absolute knowledge of the location of the cam, and if the microplate, sample cup or sample tube holder is directly coupled to the cam, then there will be an absolute knowledge of the location of the well in the plate, the sample cup or the sample tube. Thus, a polar coordinate positioning system of the disclosure allows knowledge of the precise location of an object relative to a second object such as a tool in a hysteresis free system. The cam can be shaped to generate either linear or non-linear change in motion with the angular change of the driving motor, or a combination of both, depending on the motion desired.

A further modification of a polar coordinate positioning system can be for the motor to be integrated with a microprocessor to control its motions, for example, acceleration, velocity, deceleration, torque, its location with respect to an encoder, and stall detection.

In some embodiments, a positioning system is based on polar or cylindrical coordinates. For example, an item to be positioned can be attached to the axis of rotation of a motor, where motion of the motor produces the angular displacement portion of positioning the item. In some embodiments, a second the radial portion of the displacement can be non-linear. In yet further embodiments, the radial portion of the displacement can be linear. In some embodiments, the radial portion of the displacement can be a combination of linear and non-linear motion.

This disclosure provides a system 30 for positioning a microplate 32 based on a polar coordinate system. The microplate 32 preferably includes at least one sample well 34. FIG. 1 illustrates the microplate 32 as attached to a shaft of an angular stepping motor 36. The angular stepping motor 36 is preferably configured to rotate the microplate 32 about an axis of the motor shaft an orient the microplate 32 with respect to a sampling needle 38 such that an axis defined by the sampling needle 38 is substantially aligned with the at least one sample well 34.

In some embodiments, the microplate 32 and angular stepping motor 36 are movable in at least one dimension with respect to the sampling needle 38. For example, the microplate 32 can be coupled to a linear slider 40 that permits sliding along a linear rail 42. The linear slider 40 is preferably driven by a radius stepping motor 44. In some embodiments, as illustrated in FIG. 1, the linear slider 40 is driven by the radius stepping motor 44 through an cam 46 that engages a respective cam follower 48 coupled to the linear slider 40. Accordingly, rotation of a shaft of the radius stepping motor 44 causes rotation of the cam 46, which engages the cam follower 48 and moves the linear slider 40 along the linear rail 42 as a result of an increasing or a decreasing radius of curvature of the cam 46.

In some embodiments, the linear slider 40 is configured to be biased in one direction, for example by a spring, such that the cam follower 48 is pressed against the cam 46. In some embodiments, the cam follower 48 is driven by the cam 46 in both angular rotations of the cam 46. For example, in some embodiments, the cam 46 comprises a slot or channel, in which the cam follower 48 resides such that the cam follower 48 will be forced to follow the cam 46 in both angular rotations of the cam 46.

In some embodiments, the cam 46 has a constant change in radius with angle such that rotation of the shaft of the radius stepping motor 44 is translated, through the cam 46, to a constant rate of linear motion of the linear slider 40 along the linear rail 42. Accordingly, rotation of the radius stepping motor 44 can move the microplate 32 and angular stepping motor 36 in a linear path with respect to the sampling needle 38. In some embodiments, the cam 46 is configured such that one complete rotation of the radius stepping motor 44 translates the linear slider 40 along the entire length of the linear rail 42. In such configurations, each angular position of the shaft of the radius stepping motor 44 can correlate to a particular linear location of the linear slider 40, and consequently, the sample wells 34 of the microplate 32, along the linear path defined by the linear rail 42.

In some embodiments, the sampling needle 38 is also movable along a linear path. For example, as illustrated in FIG. 1, the sampling needle 38 can be movable along a linear path that is substantially perpendicular to the linear path of the microplate 32. In some embodiments, the positioning system 30 can include a sample needle stepping motor 50 that has a shaft coupled with a stepping needle cam 52. The stepping needle cam 52 preferably engages a stepping needle cam follower 54 such that angular rotation of the cam 52 translates into a change of linear position between the motor 50 and the cam follower 54. As illustrated in FIG. 1, the sampling needle 38 is preferably coupled with the stepping motor 50 and the cam 52 such that rotation of the cam 52 against the cam follower 54 translates the sampling needle 38 and the motor 50 along a linear path that is transverse to the linear path of the microplate 32. The cam 52 and the cam follower 54 can be configured in similar manner as that described above with respect to cam 46 and cam follower 48. In some embodiments, the cams 46, 52 can be configured to produce a linear path, and in some embodiments, the cams 46, 52 can be configured to product a non-linear path.

Figure 7:
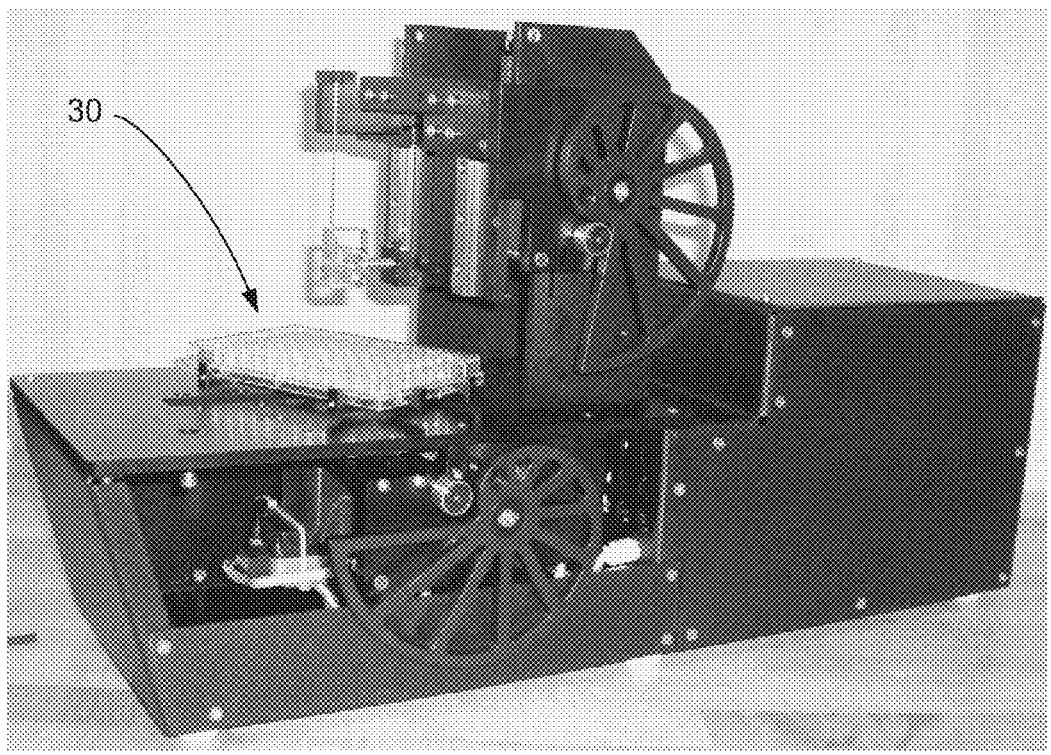
FIG. 7 depicts, in perspective view, an embodiment of the disclosure.

In some embodiments, the sampling needle 38 is translatable in a substantially vertical direction, as illustrated in FIGS. 1 and 7, and the microplate 32 is translatable in a substantially horizontal direction. The microplate 32 is further rotatable about an axis defined by the shaft of motor 36. Accordingly, the sampling needle 38 is movable along an axis defined by the needle 38 and can be drawn into and out of a plane that is defined by the microplate 32 along the axis. The microplate 32 is configured to permit angular and radial orientation by the angular rotation of the motor 36 and linear translation driven by motor 44. Accordingly, coordination between the three motors 36, 44, 50 permit the sampling needle 38 to cooperate with the microplate 32 in positioning the sampling needle 38 with respect to, for example, sample wells 34 of the microplate 32. For example, the sampling needle 38 can be lowered into a first sample well 34 and raised to be withdrawn from the well 34. The microplate 32 can be subsequently rotated and/or translated along a linear path to orient, for example, a second sampling well 34 with respect to the axis of the sampling needle 38. The sampling needle 38 may then be lowered into the second sampling well 34 and raised after taking the sample.

Figure 2:
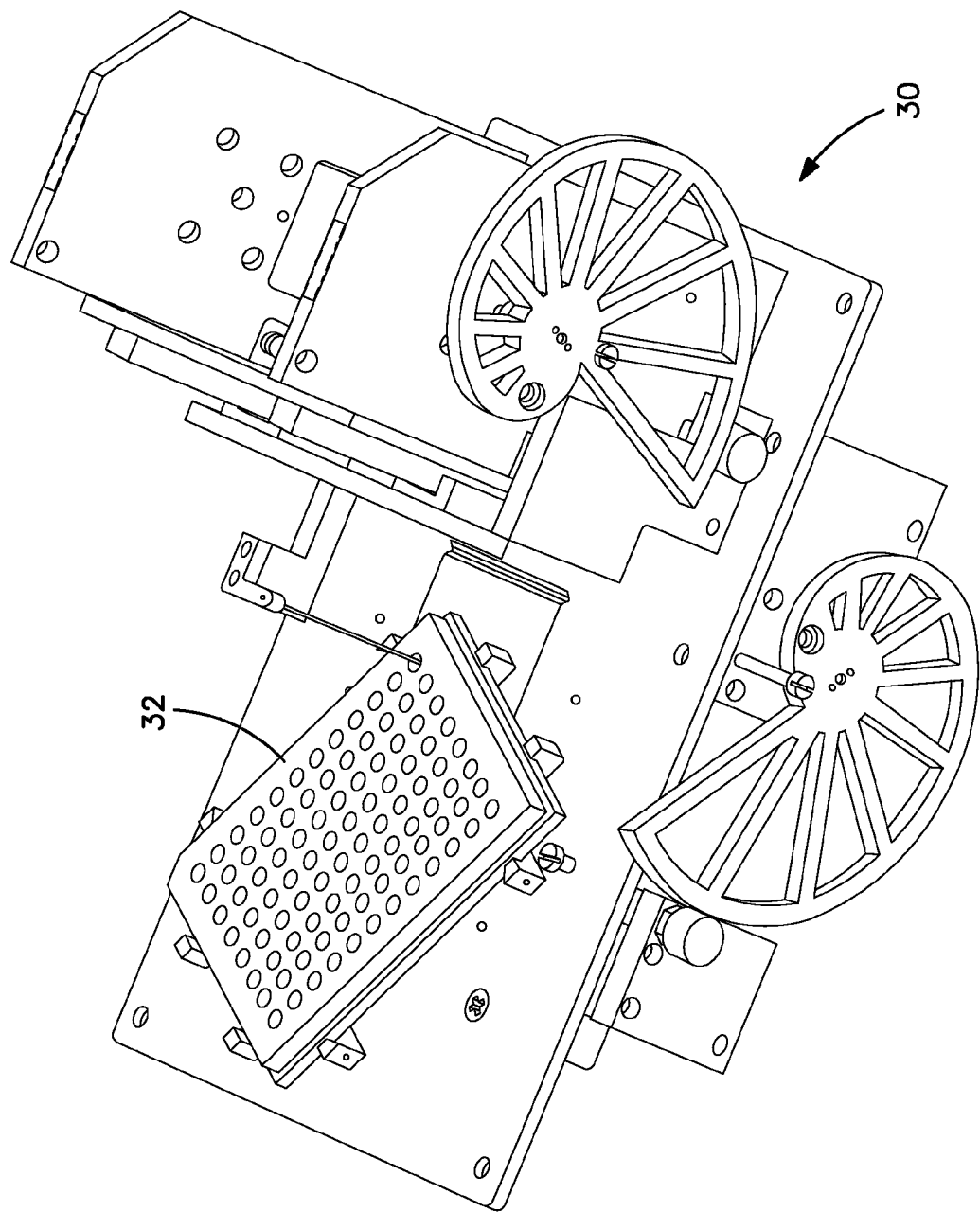
FIG. 2 illustrates an embodiment of the system depicting a microplate in a first position and orientation.
Figure 3:
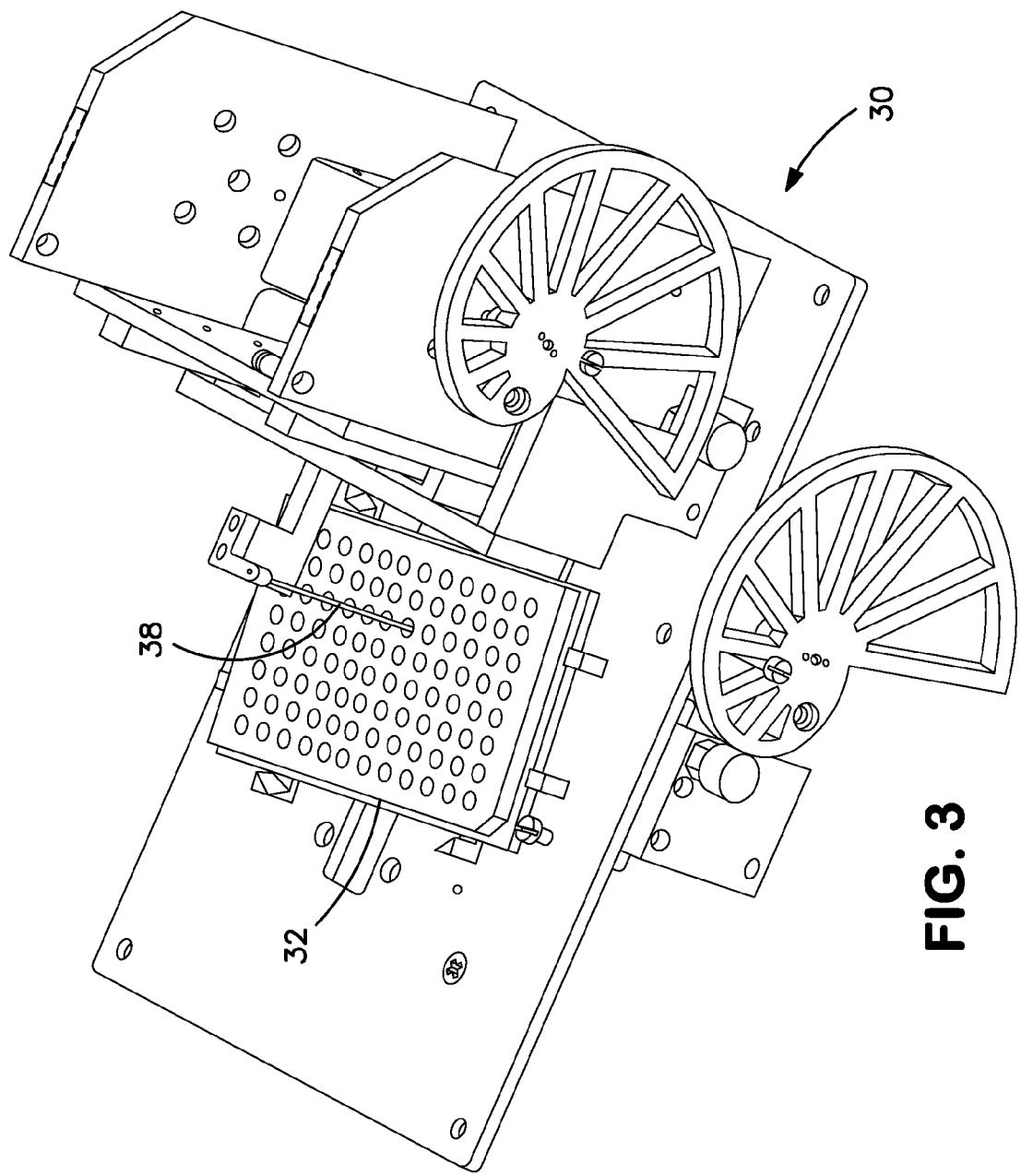
FIG. 3 illustrates an embodiment of the system depicting the microplate in a second position and orientation.
Figure 4:
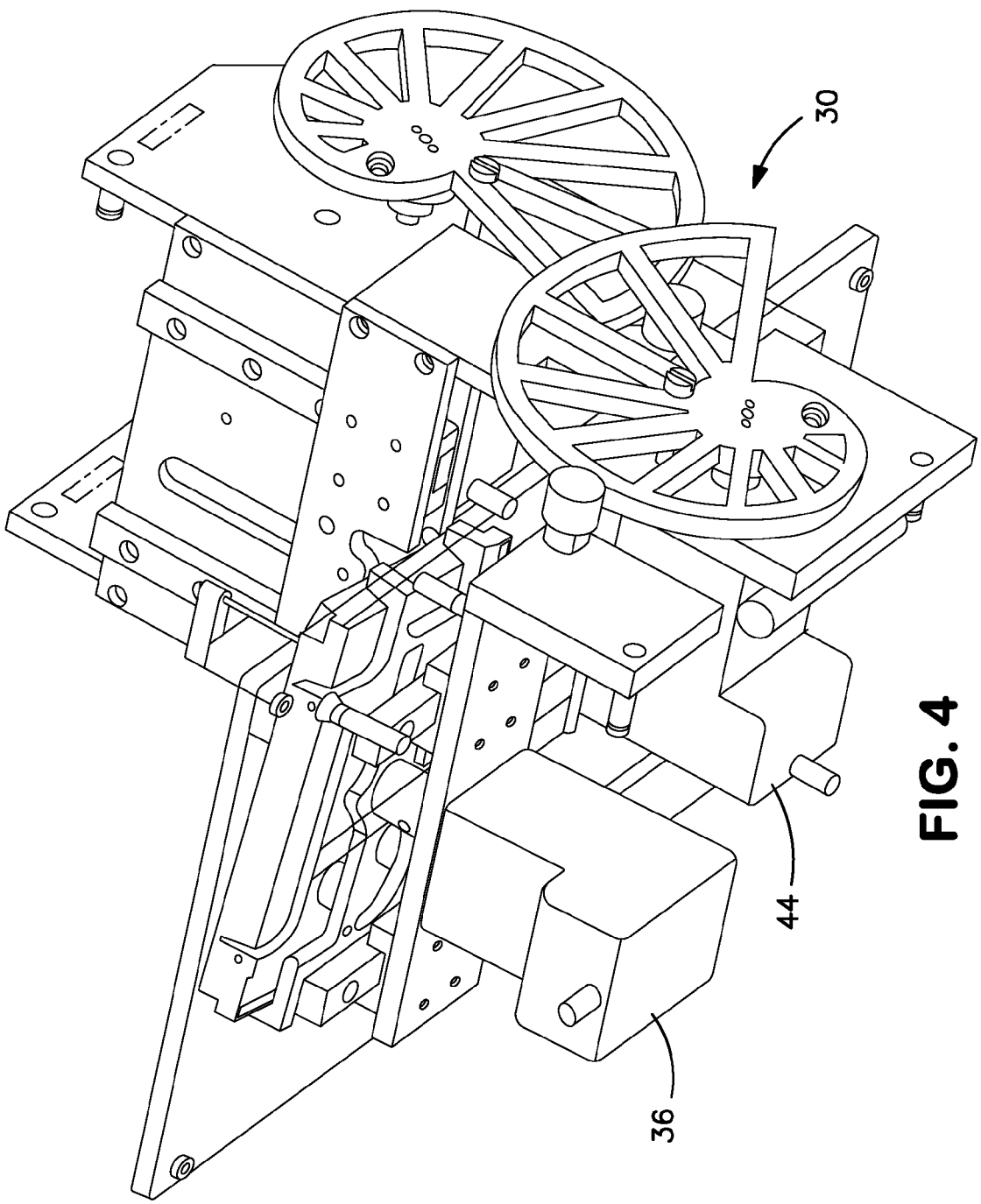
FIG. 4 illustrates an embodiment of the system that highlights details of some embodiments of a linear rail configuration and a radius stepping motor.
Figure 5:
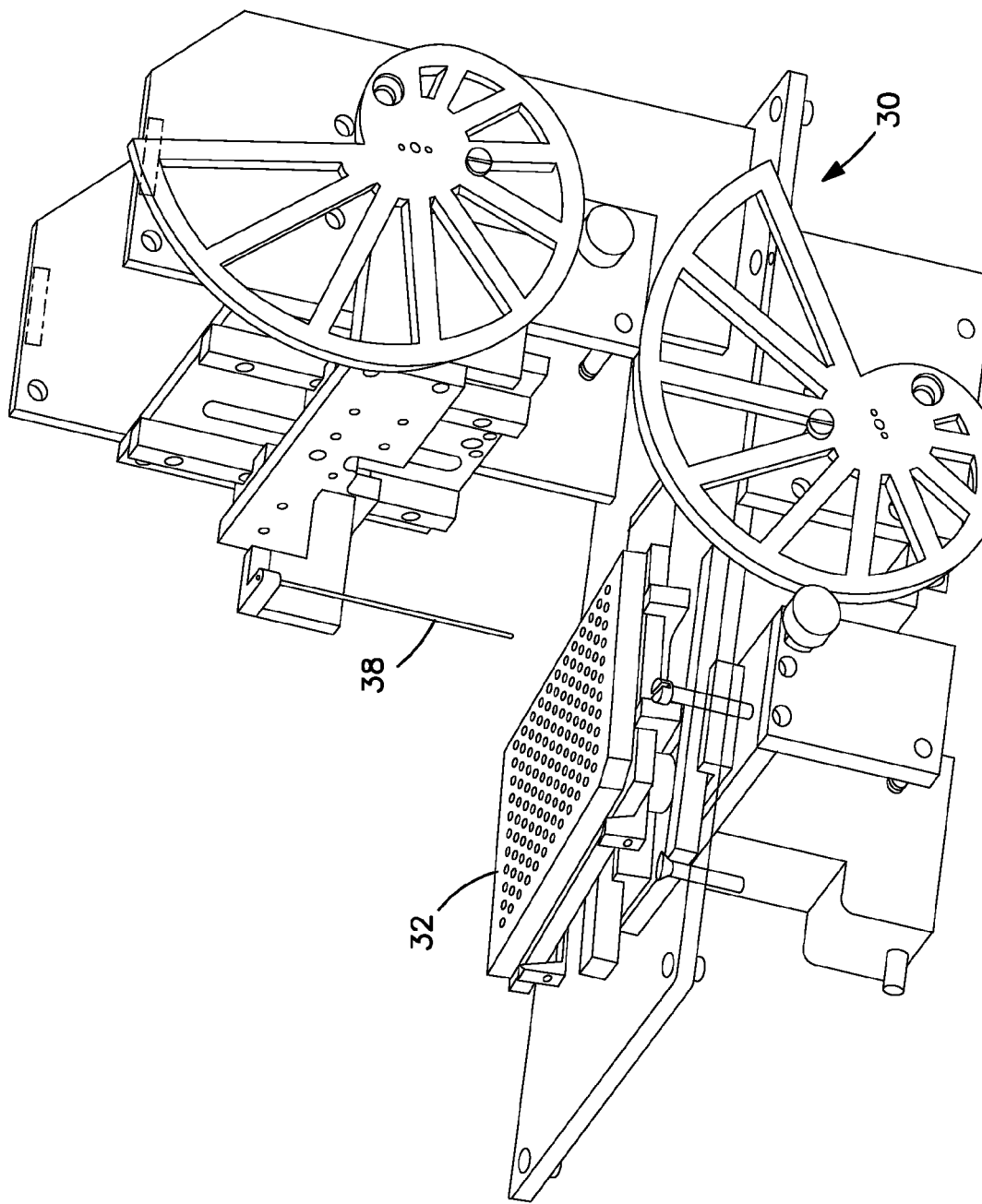
FIG. 5 illustrates a sample needle after it has been removed from a sample well.

FIG. 2 illustrates the system 30 with the microplate 32 in one position following rotation of motor 44 to translate the microplate 32 in a linear direction. FIG. 3 illustrates the system 30 with the microplate 32 in a second position in which the microplate 32 is drawn toward the sampling needle 38. FIG. 4 illustrates perspective view of an embodiment of a bottom configuration of the system 30, showing the mounting of motors 36, 44. FIG. 5 illustrates a perspective view of the system 30, showing the sampling needle 38 withdrawn from the microplate 32.

Figure 6:
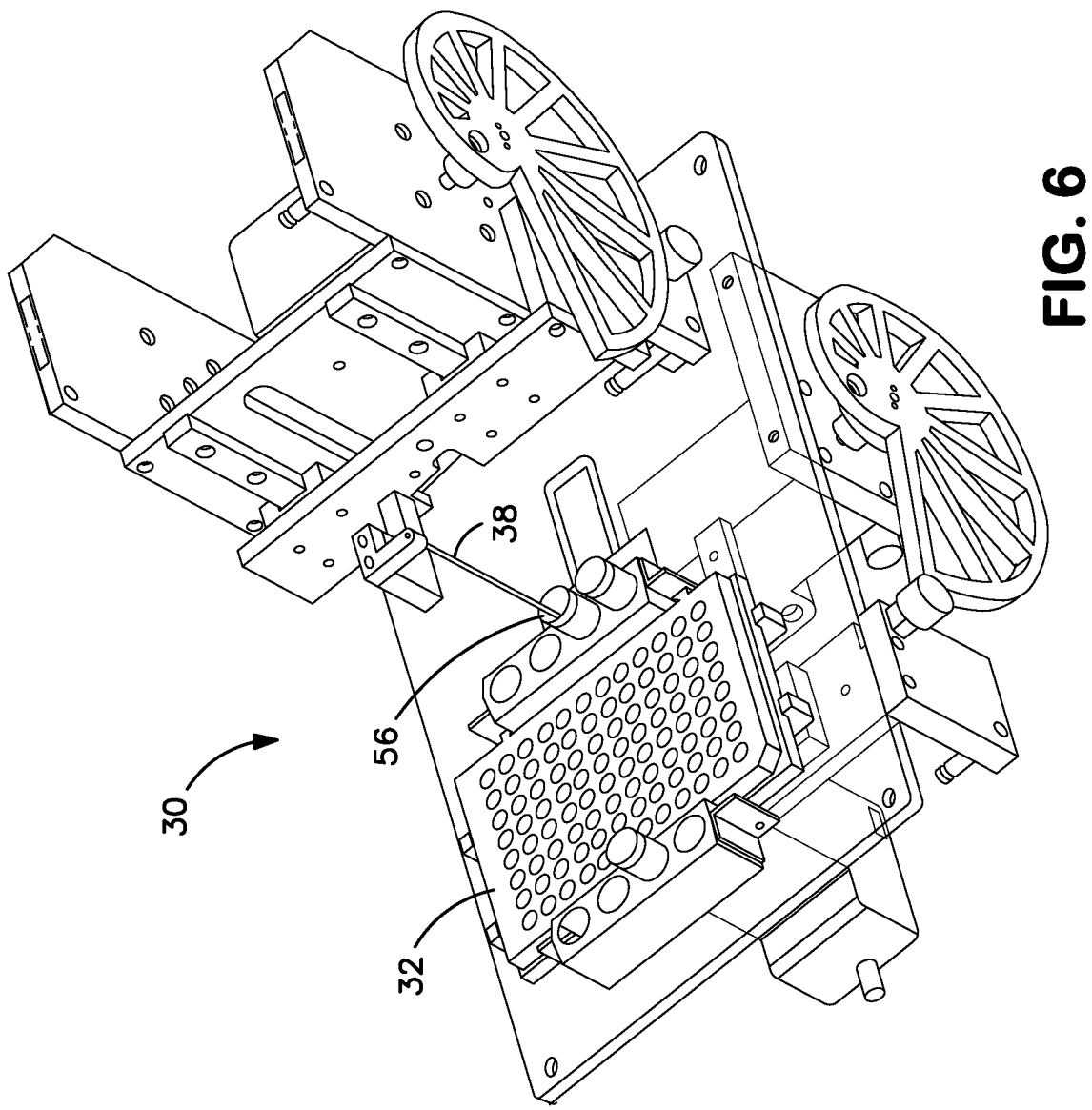
FIG. 6 illustrates the sample needle positioned in a sample tube beside the microplate.

FIG. 6 illustrates some embodiments of the system 30, in which the microplate 32 includes an attachment for placing, for example, reagent tubes 56 along a portion of the microplate 32. These embodiments can permit the system 30 to be used as a sample preparation device in addition to its use in removing samples from the sample wells 34 for analysis. In some embodiments, the sampling needle 38 is configured to extend into planes other than the plane defined by the microplate 32. For example, as illustrated in FIG. 6, the sampling needle 38 can be configured to extend into and out of planes above and below the plane of the microplate 32 for use with, for example, reagent tubes 56.

The sampling needle 38 is preferably attached to analysis instrumentation that will permit analysis of the samples taken by the sampling needle 38 from the sampling wells 34. The instrumentation can also be configured to analyze, or confirm, appropriate consistency and/or composition of other materials (e.g., material in the reagent tubes 56). As used herein, the term sample is intended to include, without limitation, samples located in sampling wells or other materials located in other containers such as, for example, reagents in reagent tubes. The sampling needle 38 is preferably configured to obtain samples from, for example, a sample tube, a sample cup, an array of sample tubes, an array of sample cups, a microplate, which may be a 24-, 96-, 384-, or a 1536-well microplate.

The motors 36, 44, 50 are preferably stepping motors that can include integral encoders and microprocessors. The motors are preferably connected to a common control that can provide instructions that are communicated to the motors to orient the microplate 32 in a specified orientation in a polar coordinate system and to position the sampling needle 38 with respect to the microplate 32. In some embodiments the motors coordinate to move the microplate 32 in, for example, a straight line, an arc, or along an irregular path. The motor microprocessors receive their commands through a RS422 data buss that connects to the common control, which may be, for example, a main system computer, through a USB to RS422 converter. Other types of well known connections for sending and receiving commands for a microprocessor can be used.

The disclosure also provides a system for positioning an item comprising a first driving means for imparting angular displacement on the item; and a second driving means for imparting radial displacement on the item. In one embodiment of a system for positioning an item, the item is one or more of a sample tube, a sample cup, an array of sample tubes, an array of sample cups, and a microplate.

The disclosure further provides a system for positioning an item relative to a tool comprising a first driving means for imparting one of angular or radial displacement on the item; and a second driving means for imparting the other of angular or radial displacement on the item.

In still another embodiment, the disclosure provides a method for positioning an item from a first position to a second position by rotating the item to provide angular displacement of the item; and moving the item linearly to provide radial displacement of the item. The method can be repeated for serial acquisition of samples from the moved item.

In one embodiment, the object that is being positioned, for example, a microplate or sample tube, is rotated to produce one of the displacements, and a second motion of the object is produced in the plane by either a rotational or linear motion producing the second displacement. These motions will uniquely position the object with respect to a tool having a fixed location in the plane.

Although exemplified herein as a microplate reader, it is understood that a polar coordinate positioning system of the disclosure can be for any use in which it is desired to position one object relative to a second object such as a tool. For example, a tool can be a sample needle if the object is a microplate or sample tube. A tool can also be a riveting tool if the object is to be attached to a second object, such as when a rhinestone is attached to material such as leather or cloth. Additionally, a tool can be a microscope objective if the object is a microscope slide being observed. A tool can also be a laser used to cut, mark or illuminate an object. These examples do not limit what the tool is or the application of the positioning system. A tool can be any thing which measures, samples, illuminates, dispenses into, or changes the object in any way.

In another embodiment, the object that is being positioned is rotated only to produce one of the displacements. The tool is then moved either in an arc or a line in the plane to produce the second displacement. These motions will uniquely position the object with respect to some moving tool.

In still another embodiment, the rotation of the object is performed in conjunction with linear motion of either the object or the tool, where the linear motion is either a lead screw, belt, pulley, cable, linear actuator, cam or some other motion producing device. This linear motion is not simply the moving of the object from some load point to a sampling position, but the motion necessary to move the object from tube to tube, micro well to micro well, cup to cup or point to point, after loading of the object has been accomplished.

In an embodiment of the disclosure using a cam, the cam has either linear or non linear displacement or some combination thereof with respect to its center of rotation. In another embodiment, the cam can be attached to a motor with sufficient angular resolution to produce the desired motion in less than or equal to one rotation.

In yet another embodiment of the disclosure, the motors, for the object rotation or the cam rotation, can include an encoder to determine the angular displacement. In another embodiment, the motors, for the object rotation or the cam rotation, can have a processor either external or internal to control its motions, for example, acceleration, velocity, deceleration, torque, stall detection and the like.

A polar coordinate positioning system of the disclosure can be used for positioning objects having a variety of configurations. For example, an object to be positioned can be a sample tube, a sample cup, an array of sample tubes, an array of sample cups, or a microplate of various configurations, including, for example, a 24 well microplate, a 96 well microplate, a 384 well microplate, a 1536 well micro plate, or other configurations.

In still another embodiment of the disclosure, a polar coordinate positioning system can use rotational motion only using a motor with an internal processor, also referred to as an intelligent motor, for rotation of a microplate or sample tubes. An exemplary intelligent motor includes the MDRIVE™ Plus series of intelligent motors from Intelligent Motion Systems, Inc. (Marlborough Conn.), as described in MDrive Plus Motion Control Hardware Reference, the entirety of which is hereby incorporated by reference. Such a motor can be useful because it has the ability to detect motor stalling, making the device practical and enhancing its operation. For example, a sipper needle can detect if a well is missed and report the error without destroying the needle.

It is understood that modifications which do not substantially affect the activity the various embodiments of this disclosure are also provided within the definition of the disclosure provided herein. Although the disclosure has been described with reference to the description above, it should be understood that various modifications can be made without departing from the spirit of the disclosure.

What is claimed is:

1. A positioning system, based on polar or cylindrical coordinates, comprising:
   a sampling needle for obtaining a sample; and,
   a sampling tray that comprises at least one sampling well, the sampling tray being movable in a first direction, the sampling tray further being movable in a second direction that is transverse to the first direction;
   wherein the sampling needle is configured to obtain the sample from the at least one sampling well and the sampling tray is oriented and positioned with respect to an angular displacement about an axis and an angular displacement from an origin.

2. The positioning system of claim 1, wherein the sampling tray is rotatable about an axis that is transverse to at least one of the first and second direction.

3. The positioning system of claim 1, wherein the sampling tray is movable with respect to the sampling needle.

4. A positioning system, based on polar or cylindrical coordinates, comprising:
   a sampling needle for obtaining a sample; and,
   a sampling tray that comprises at least one sampling well, the sampling tray being movable in a first direction, the sampling tray further being movable in a second direction that is transverse to the first direction;
   wherein the sampling needle is configured to obtain the sample from the at least one sampling well and the sampling tray is oriented and positioned with respect to a first angular displacement about a first axis and a second angular displacement about a second axis.

5. The positioning system of claim 4, wherein the sampling tray is rotatable about at least one of the first and the second axis.

6. The positioning system of claim 4, wherein the sampling tray is movable with respect to the sampling needle.

* * * * *